(12) United States Patent
Griffin et al.

(10) Patent No.: US 8,841,632 B1
(45) Date of Patent: Sep. 23, 2014

(54) REMOVABLE DENTAL APPLIANCE SANITIZER AND STORAGE DEVICE

(75) Inventors: Bradley P. Griffin, Greenville, NC (US); Gary Fisher, Kowloon Bay (HK)

(73) Assignee: Practicon, Inc., Greenville, NC (US)

( * ) Notice: Subject to any disclaimer, the term of this patent is extended or adjusted under 35 U.S.C. 154(b) by 402 days.

(21) Appl. No.: 13/175,262

(22) Filed: Jul. 1, 2011

Related U.S. Application Data

(60) Provisional application No. 61/398,914, filed on Jul. 2, 2010.

(51) Int. Cl.
*H01J 37/20* (2006.01)

(52) U.S. Cl.
USPC ............ 250/455.11; 250/453.11; 250/454.11; 250/493.1; 250/494.1; 250/504 R

(58) Field of Classification Search
USPC ............... 250/453.11, 454.11, 455.11, 493.1, 250/494.1, 504 R
See application file for complete search history.

(56) References Cited

U.S. PATENT DOCUMENTS

| | | | |
|---|---|---|---|
| 2,253,250 | A | 8/1941 | Selig |
| D257,790 | S | 1/1981 | Kesling |
| 4,327,060 | A | 4/1982 | Nisii |
| D287,628 | S | 1/1987 | Schiavo et al. |
| D372,535 | S | 8/1996 | DiCianna et al. |
| 5,636,379 | A | 6/1997 | Williams |
| D413,986 | S | 9/1999 | Lin |
| 6,305,591 | B1 | 10/2001 | Jones |
| 6,417,761 | B1 | 7/2002 | Elliott |
| D493,578 | S | 7/2004 | Manzo et al. |
| D500,895 | S | 1/2005 | Manzo et al. |
| D523,994 | S | 6/2006 | Manzo |
| 7,063,822 | B2 | 6/2006 | Goertz et al. |
| D525,749 | S | 7/2006 | Manzo et al. |
| D526,093 | S | 8/2006 | Manzo et al. |
| D526,095 | S | 8/2006 | Manzo et al. |
| D527,848 | S | 9/2006 | Manzo et al. |
| D530,863 | S | 10/2006 | Manzo et al. |
| D532,559 | S | 11/2006 | Manzo et al. |
| D537,986 | S | 3/2007 | Manzo et al. |
| D537,987 | S | 3/2007 | Manzo et al. |
| D548,403 | S | 8/2007 | Manzo et al. |

(Continued)

FOREIGN PATENT DOCUMENTS

CA 2251672 8/1998

OTHER PUBLICATIONS

Website: www.violight.com—Dental Spa—copyright 2007 Violight, Inc.
Website—BNH International, Inc.—Mar. 24, 2006 UV Denta.

(Continued)

*Primary Examiner* — Jack Berman
*Assistant Examiner* — Meenakshi Sahu
(74) *Attorney, Agent, or Firm* — Nelson Mullins Riley & Scarborough LLP

(57) ABSTRACT

A device having a vertical slot for sanitizing a dental appliance inserted in the device. The device comprises a removable tray for containing a dental appliance, the removable tray is suitable to be lifted in and out of the vertical slot of the sanitizing device. The device comprises vertically extending walls on opposing sides of the vertical slot between which the removable tray is inserted, wherein one of the vertically extending walls comprises an ultraviolet lamp for transmission of ultraviolet light.

18 Claims, 18 Drawing Sheets

(56) References Cited

U.S. PATENT DOCUMENTS

| | | |
|---|---|---|
| D563,561 S | 3/2008 | Faust, III et al. |
| D584,417 S | 1/2009 | Massee |
| D661,812 S | 6/2012 | Griffin |
| 2008/0131330 A1 | 6/2008 | Lyon et al. |
| 2008/0219883 A1 | 9/2008 | Thur et al. |
| 2009/0010826 A1* | 1/2009 | Shin ............................ 422/300 |
| 2010/0044582 A1* | 2/2010 | Cooper et al. ........... 250/455.11 |
| 2010/0143188 A1 | 6/2010 | Roiniotis |

OTHER PUBLICATIONS

Website: www.brainpads.com—Feb. 4, 2009.

* cited by examiner

REMOVABLE DENTAL APPLIANCE SANITIZER AND STORAGE DEVICE

CROSS-REFERENCE TO RELATED APPLICATIONS

This application claims the benefit of U.S. Provisional Patent Application No. 61/398,914, filed Jul. 2, 2011, herein incorporated by reference in its entirety.

FIELD OF THE INVENTION

The present invention relates to a device for sanitizing a dental appliance, more particularly to a device for sanitizing a removable dental appliance.

BACKGROUND OF THE INVENTION

The American Association of Orthodontists (AAO) estimates that more than four million people in the U.S. are wearing braces at any one time. With improvements in the appearance and comfort of braces, and with a trend towards maintaining and improving one's natural smile as the population ages, adult orthodontics is growing rapidly. After orthodontic treatment, patients must wear a retainer or else risk having their teeth "drift" back into malocclusion. With an average treatment period of 26 months, approximately 1.8 million people graduate into removable retainers, a type of dental appliance, every year. Given that former orthodontic patients are recommended to wear their retainers indefinitely following braces, many millions of former orthodontic patients are in the habit of wearing a retainer nightly. Even if they only wear their retainer for seven years after treatment on average, this number equals 12.6 million patients in the U.S. using orthodontic retainers at any one time. For reasons stated above, this number is likely to grow.

The popularity of clear dental appliances or aligners to move teeth is making orthodontic treatment with removable retainer-like devices extremely common. Many manufacturers of this treatment technology now exist, and both orthodontic specialists and general dentists are delivering it. Other removable dental appliances such as bleaching trays, mouth guards, night guards and partial dentures greatly increase the number people in the U.S. wearing removable dental appliances.

However, use of such dental appliances creates problems for users of such appliances in terms of maintenance and sanitization of the device. Users of dental appliances typically just rinse their dental appliances and set them in a plastic case or on the edge of the sink. Germs from both the mouth and the environment gather and breed on them invisibly. Unlike toothbrushes, dental appliances can cost $200 to $500 to replace. It is not cost effective to just throw them away after an illness or when they do not look new. There is not a simple, standard way to keep dental appliances sanitary on a daily basis. Brushing them with a toothbrush only transfers more germs to their surface. Boiling them can deform their plastic construction. There are cleaning tablets and powders available, but they are not widely used due to their messiness and expense, and many do not disinfect the dental appliance but only deodorize them. Thus, there is a need for a device for sanitizing removable dental appliances.

SUMMARY OF THE INVENTION

The present invention is directed to a device for sanitizing a removable dental appliance. The device comprises a vertical slot for insertion of a removable dental appliance in the sanitizing device and vertically extending walls on opposing sides of the vertical slot, wherein one of the vertically extending walls comprises an ultraviolet lamp.

As another feature of the device of the present invention, the device comprises a vertical slot in a sanitizing device, a removable tray for containing a removable dental appliance, the removable tray to be lifted in and out of the vertical slot of the sanitizing device, and vertically extending walls on opposing sides of the vertical slot between which the removable tray is inserted, wherein one of the vertically extending walls comprises an ultraviolet lamp.

In still yet another aspect of the present invention, the device comprises a vertical slot in a sanitizing device, a removable tray for containing a removable dental appliance, the removable tray to be lifted in and out of the vertical slot of the sanitizing device, and vertically extending walls between which the removable tray is inserted, wherein one of the vertically extending walls comprises an ultraviolet lamp in a U-shaped configuration, preferably an inverted U-shaped configuration.

Another aspect of the present invention relates to a removable tray for use in a dental appliance sanitizing device. The removable tray is used for containing the dental appliance. The removable tray has a bottom and at least two sides, wherein at least one of the sides of the removable tray has a reflective surface. In another aspect of the present invention, at least one of the sides of the removable tray comprises a multi-dimensional geometric pattern. In yet another aspect of the invention, at least one of the sides of the removable tray comprises at least one opening. In still yet another aspect of the present invention, the removable tray is in a U-shaped configuration.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, which are not necessarily to scale, wherein.

DETAILED DESCRIPTION OF THE INVENTION

The device of the present invention is a device for sanitizing a removable dental appliance. Examples of removable dental appliances suitable for use in the device of the present invention include, but are not limited to, bleaching or whitening trays, mouth guards, night guards, partial dentures, orthodontic retainers, and orthodontic aligners. The device of the present invention comprises a vertical slot for insertion of a removable dental appliance in a sanitizing device and vertically extending walls on opposing sides of the vertical slot, wherein one of the vertically extending walls comprises an ultraviolet (UV) lamp that emits UV light to destroy harmful bacteria and micro-organisms residing on the surfaces of the dental appliance. The following detailed description of the embodiment(s) is merely exemplary in nature and is in no way intended to limit the invention, its application, or uses.

Figure 1:
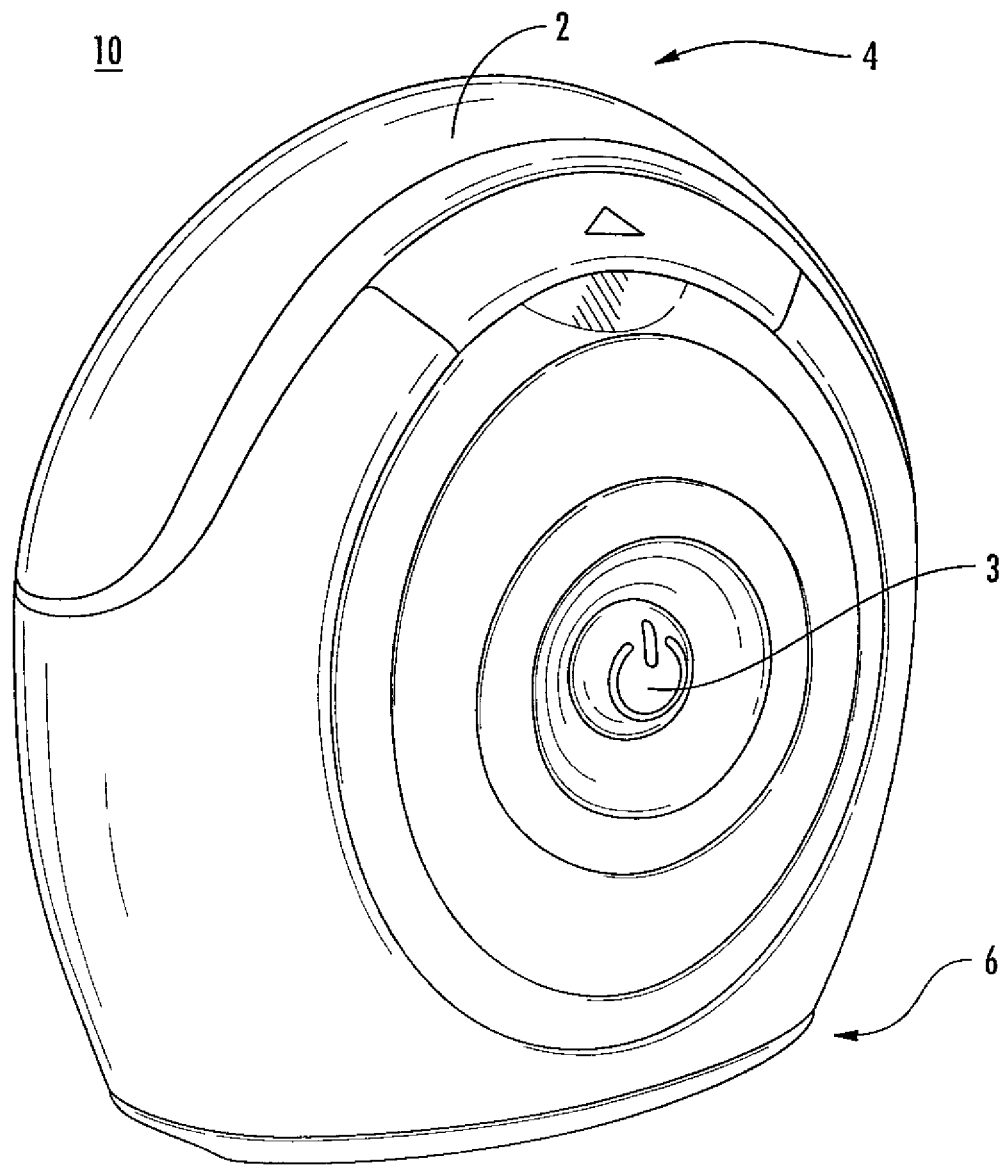
FIG. 1 is an angled front perspective view of a sanitizing device in accordance with the present invention.

Referring to the figures, FIG. 1 is an angled front perspective view of the sanitizing device of the present invention.

As shown in FIG. 1, the sanitizing device 10 preferably comprises a lid 2 that is located at the top 4 of the sanitizing device 10. The bottom 6 of the device 10 is also shown in FIG. 1. The device 10 shown in FIG. 1 is shown with the lid 2 closed.

Figure 2:
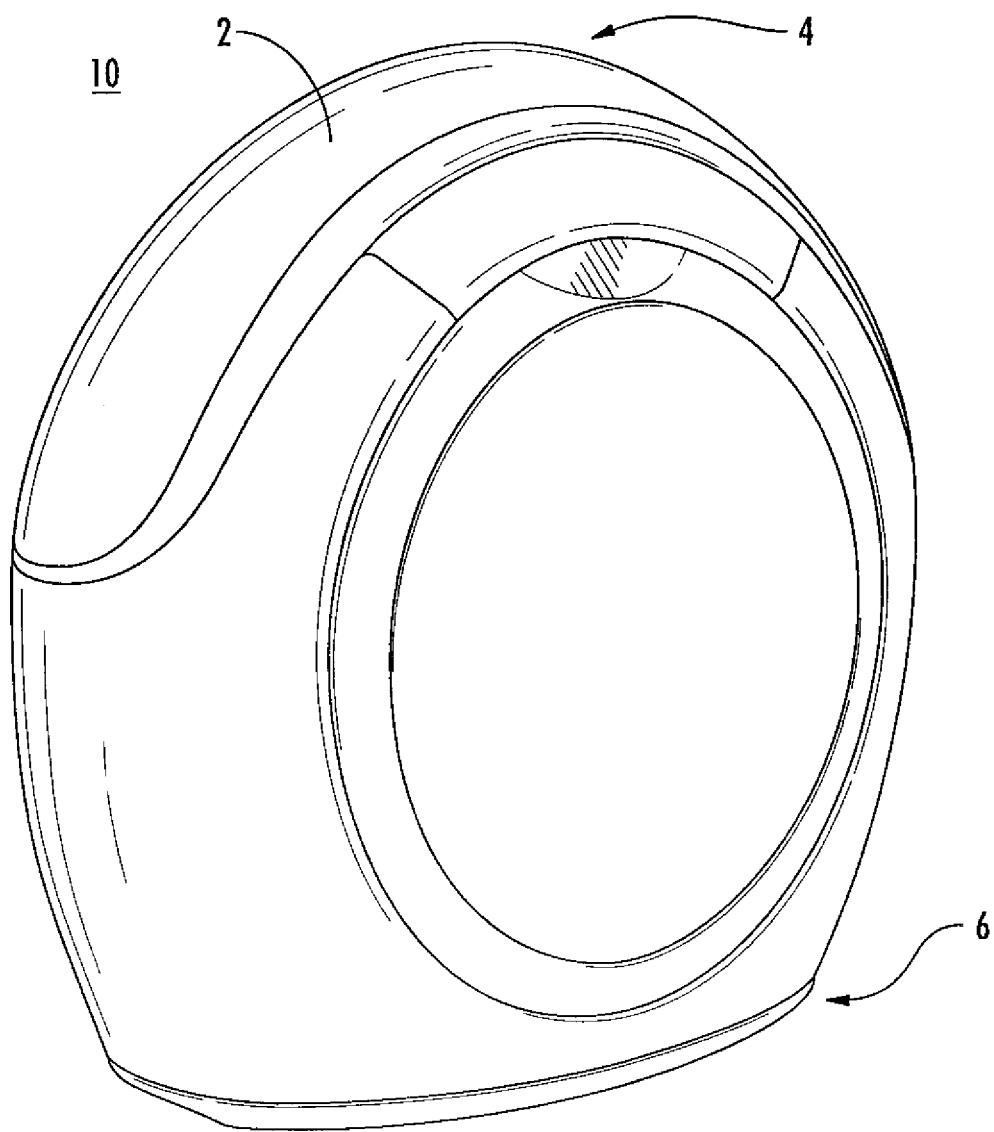
FIG. 2 is an angled back perspective view of the sanitizing device of FIG. 1.

FIG. 2 is an angled back perspective view of the sanitizing device 10 of the present invention. FIG. 2 illustrates the top 4 of the device 10, the bottom 6 of the device 10, and the lid 2 as shown from the back of the device.

Figure 3:
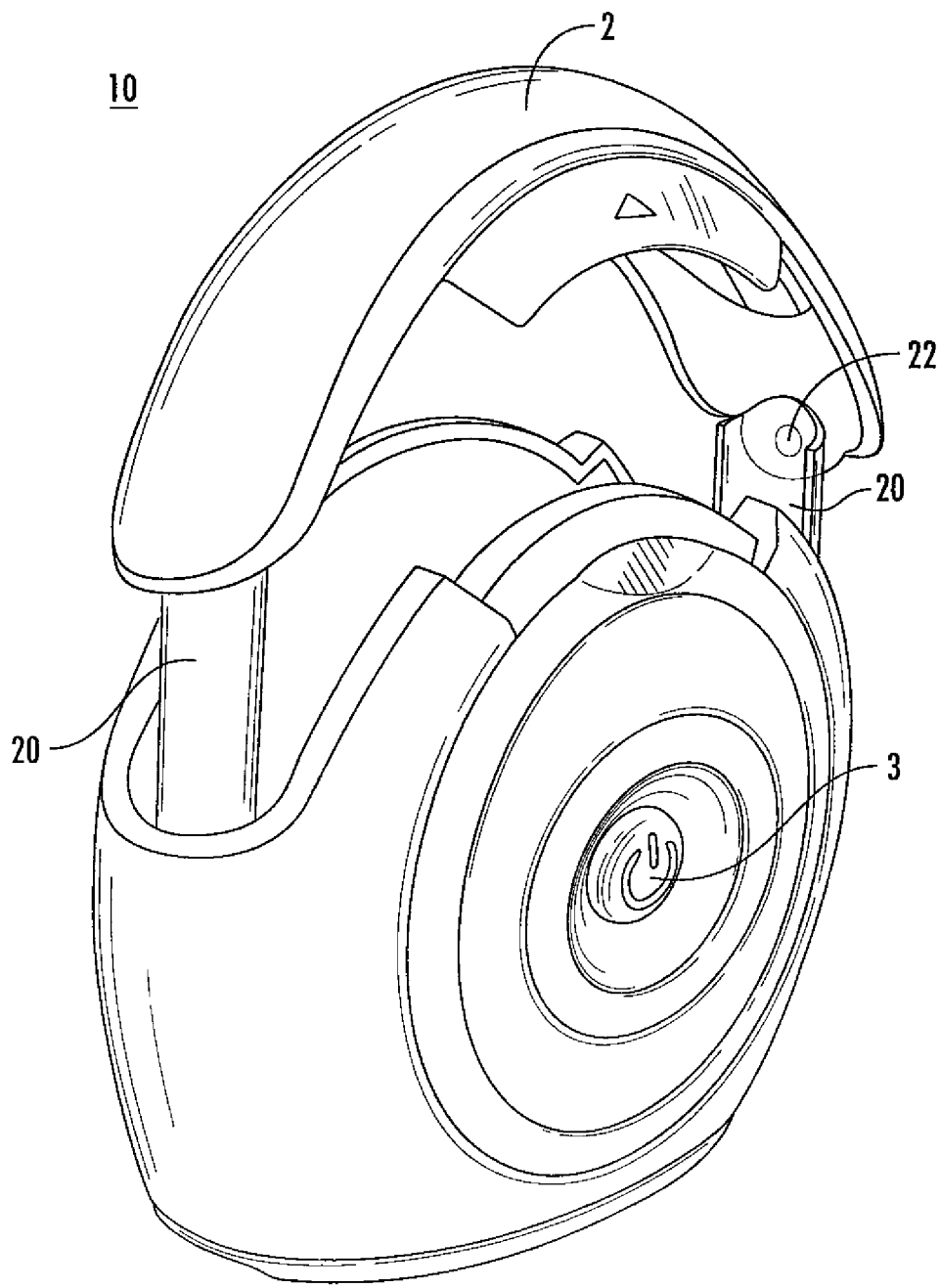
FIG. 3 is an angled front perspective view of the sanitizing device in accordance with the present invention, wherein the device has an upright open lid.

FIG. 3 is an angled front perspective view of the sanitizing device 10 of the present invention, wherein the device has an upright open lid 2. As shown in FIG. 3, the lid 2 is preferably connected to a set of retractable connecting arms 20 that permit the lid 2 to be lifted in an upright open position yet remain connected to the device. As shown in FIG. 3, each of the retractable connecting arms 20 comprises a hinge 22 that can be used to pivot the lid 2 in a forward direction and in a backward direction.

Figure 4A:
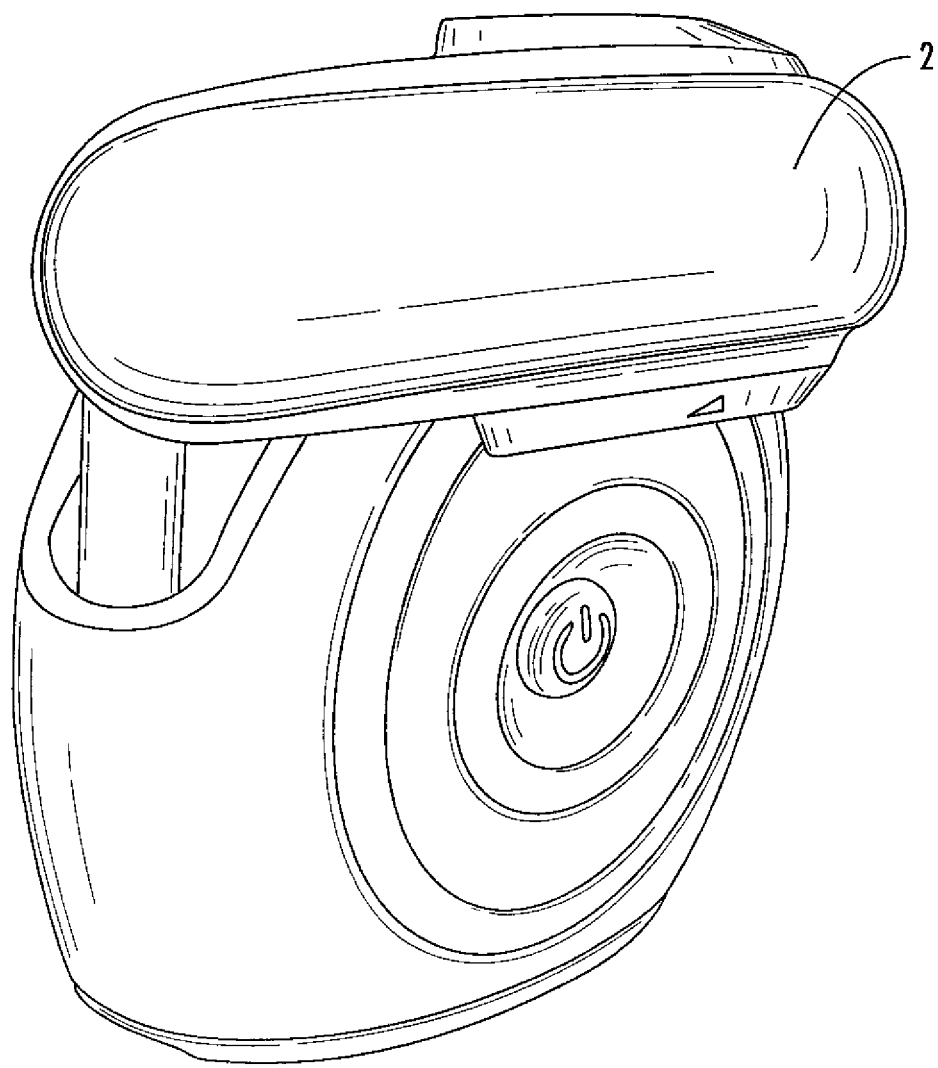
FIG. 4A is an angled front perspective view of the sanitizing device of the present invention, wherein the device has an upright open lid pivoted to the front of the device.
Figure 4B:
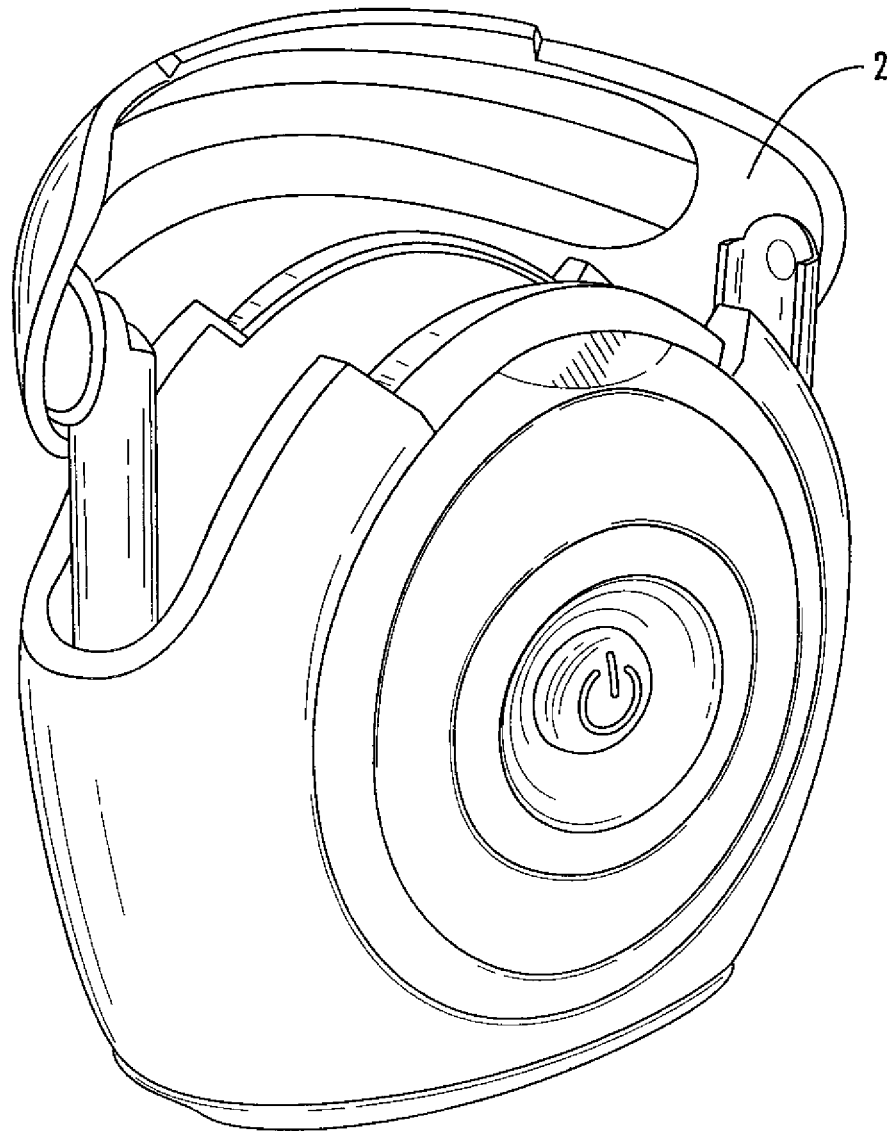
FIG. 4B is an angled front perspective view of the sanitizing device of the present invention, wherein the device has an upright open lid pivoted to the back of the device.

FIG. 4A is an angled front perspective view of the sanitizing device 10 of the present invention, wherein the device 10 has an upright open lid 2 pivoted to the front of the device 10. FIG. 4B is an angled front perspective view of the sanitizing device 10 of the present invention, wherein the device 10 has an upright open lid 2 pivoted to the back of the device 10.

Figure 5:
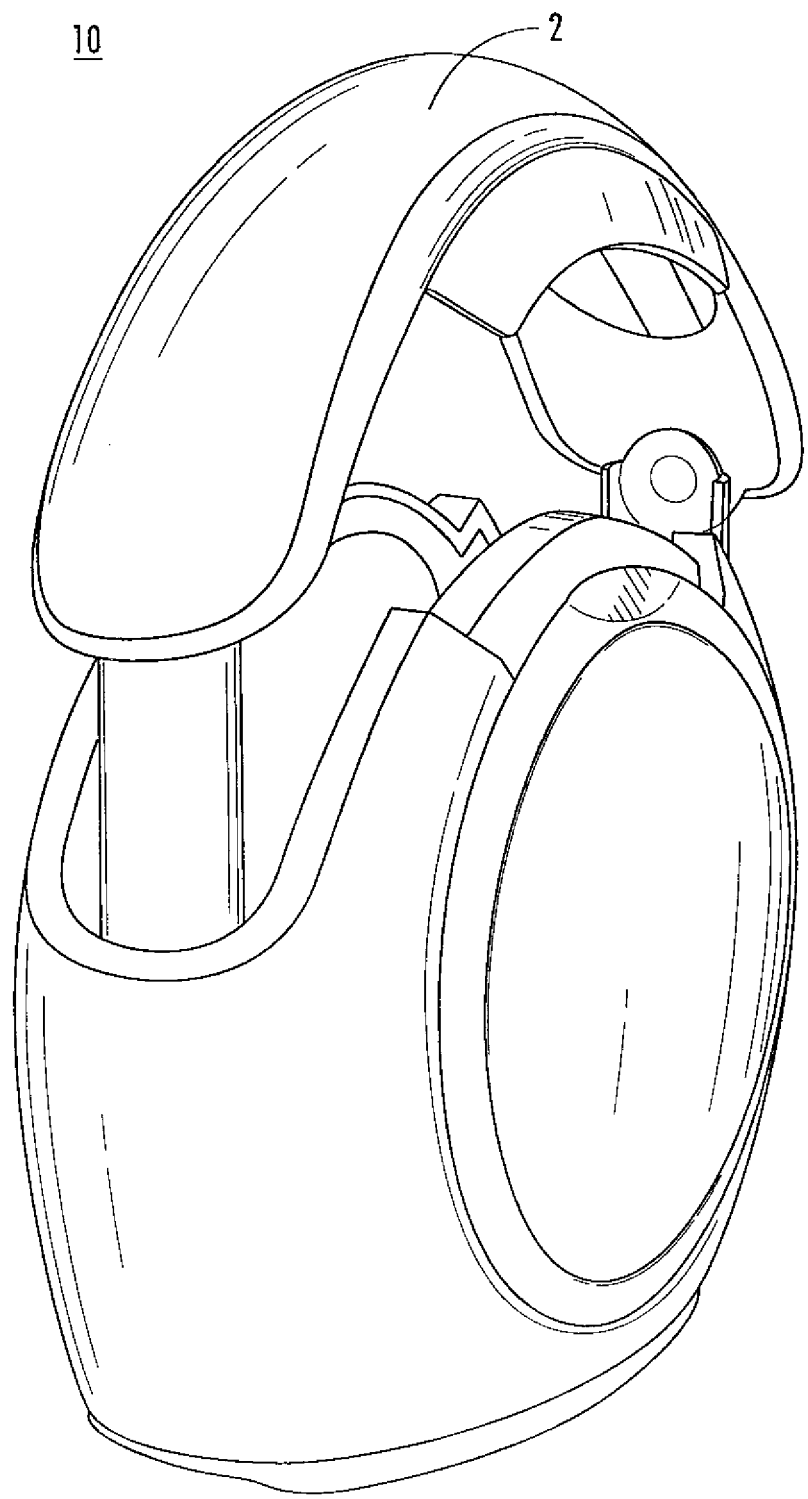
FIG. 5 is an angled back perspective view of the sanitizing device of the present invention, wherein the device has an upright open lid.
Figure 6A:
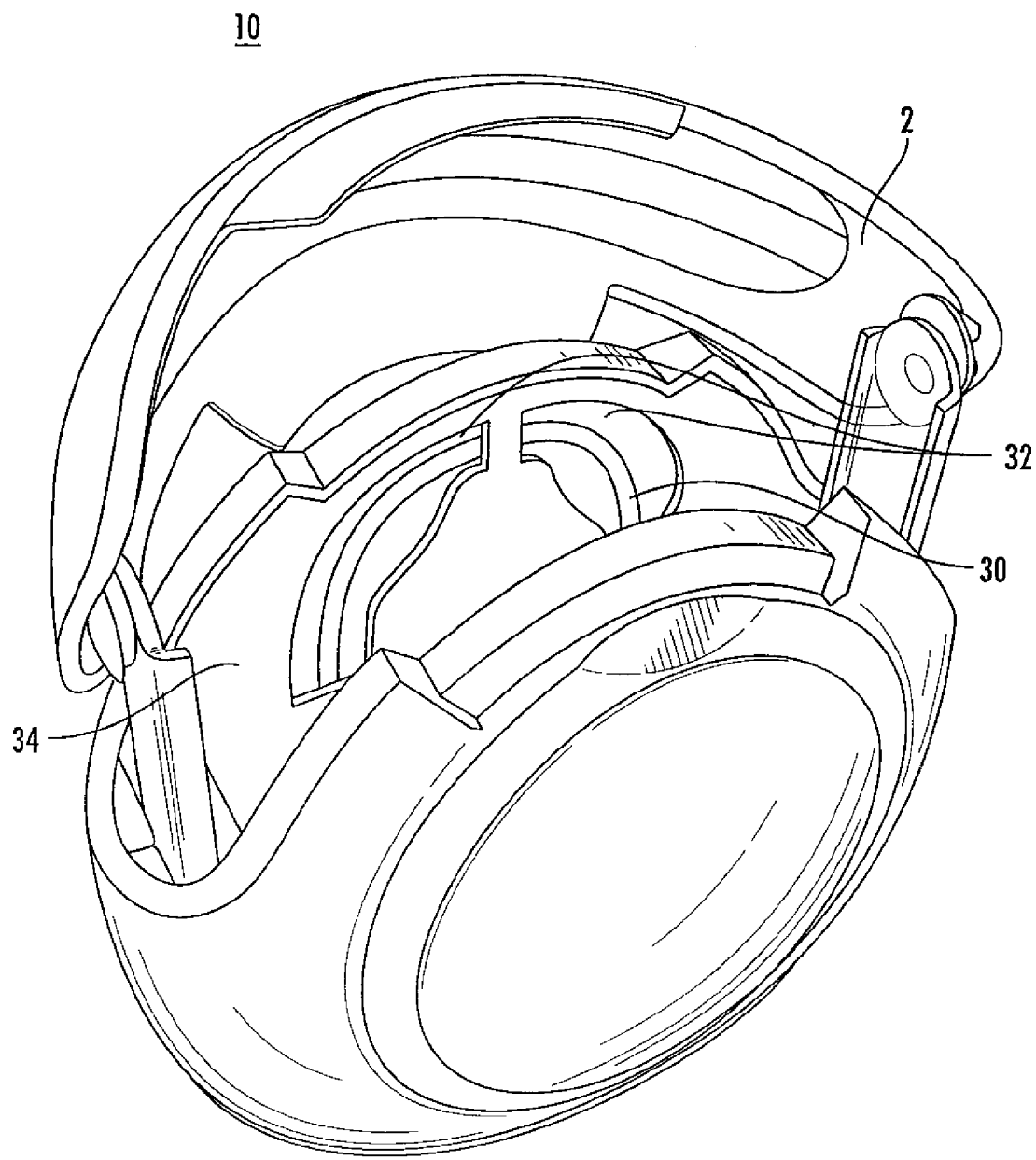
FIG. 6A is an angled back perspective view of the sanitizing device of the present invention, wherein the device has an upright open lid pivoted to the front of the device.
Figure 6B:
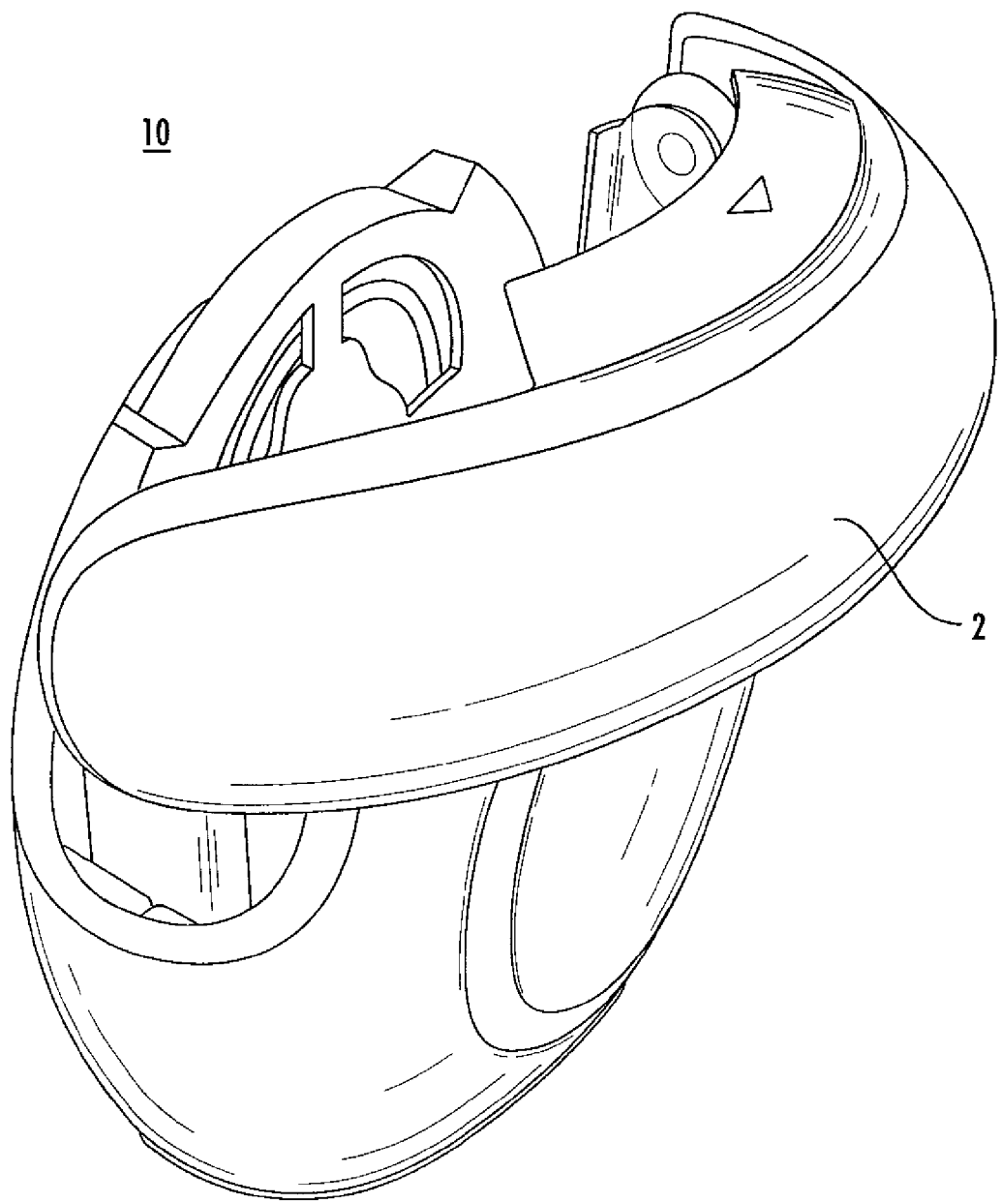
FIG. 6B is an angled back perspective view of the sanitizing device of the present invention, wherein the device has an upright open lid pivoted to the back of the device.

FIG. 5 is an angled back perspective view of the sanitizing device 10 of the present invention, wherein the device 10 has an upright open lid 2. FIG. 6A is an angled back perspective view of the sanitizing device 10 of the present invention, wherein the device 10 has an upright open lid 2 pivoted to the front of the device 10. FIG. 6A also clearly shows the UV lamp 30 in an inverted U-shaped configuration with openings 32 in the front wall 34 of the device 10 through which light from the UV lamp 30 is emitted. FIG. 6B is an angled back perspective view of the sanitizing device 10 of the present invention, wherein the device 10 has an upright open lid 2 pivoted to the back of the device 10. In an aspect of the present invention, the inner side of the lid comprises a reflective surface.

Figure 7A:
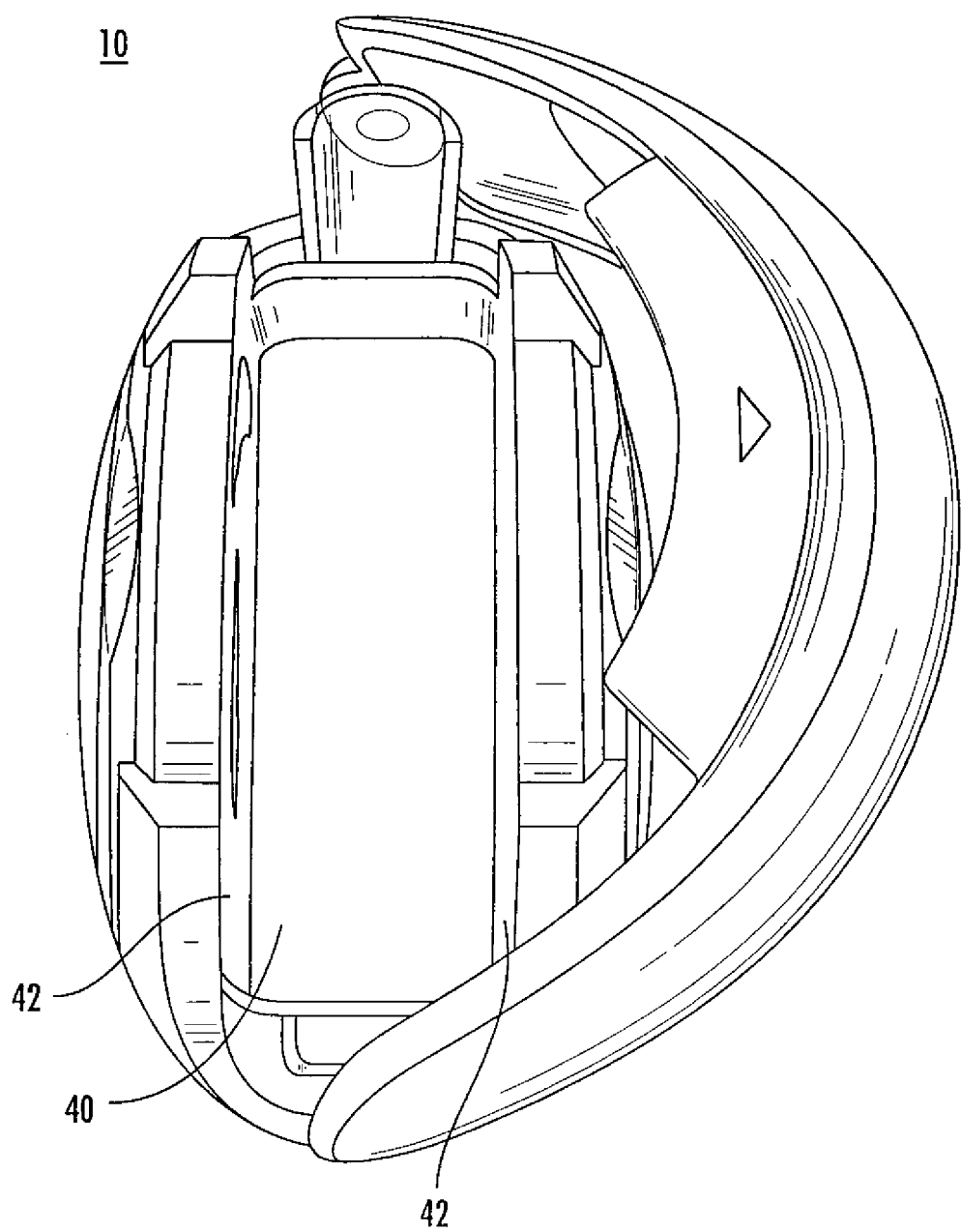
FIG. 7A is a top view of the sanitizing device of the present invention.
Figure 7B:
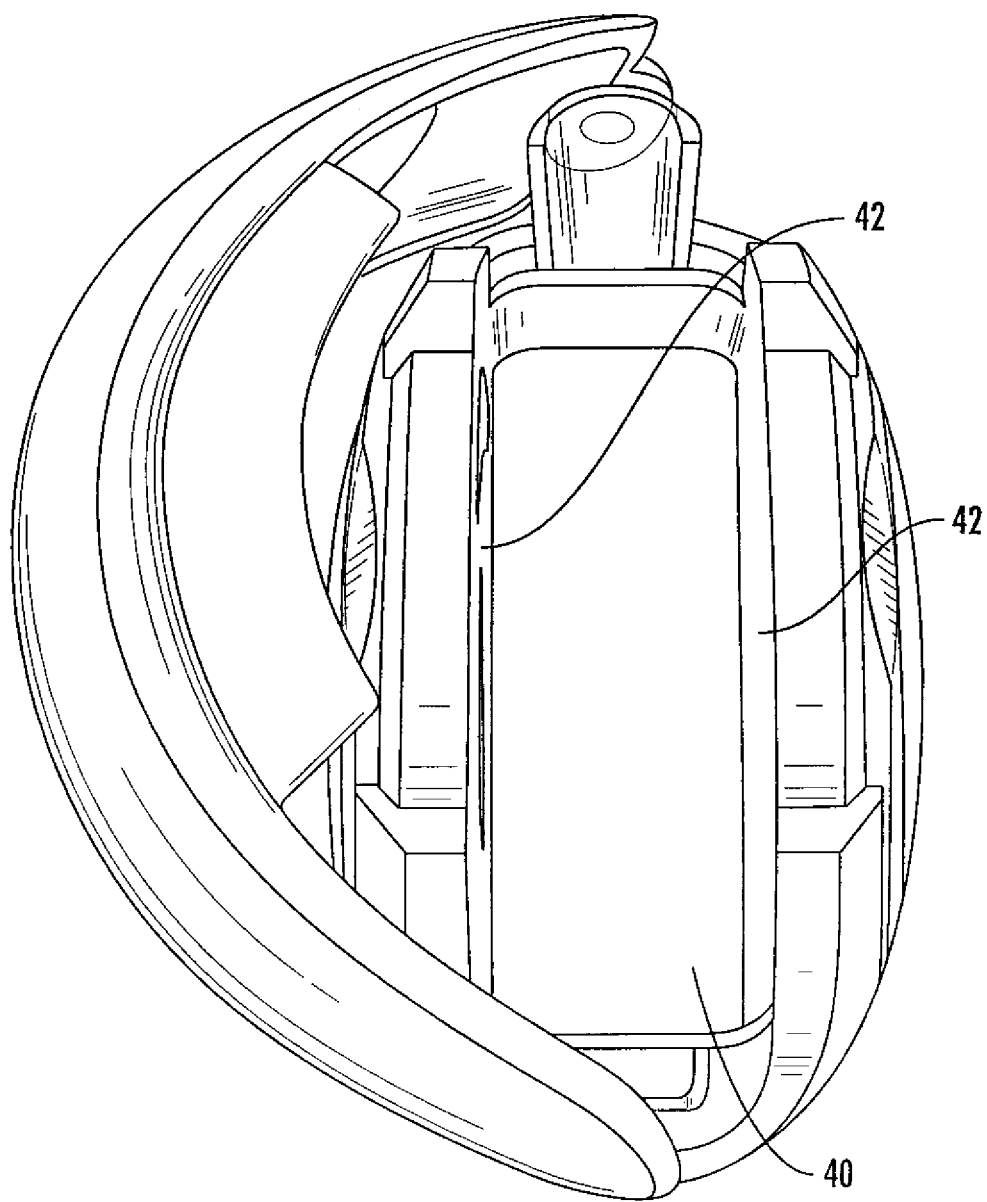
FIG. 7B is another top view of the sanitizing device of the present invention.

As shown in FIGS. 7A and 7B, the device 10 comprises a vertical slot 40 for insertion of a removable dental appliance in the sanitizing device 10 and vertically extending walls 42 on opposing sides of the vertical slot 40, wherein one of the vertically extending walls 42 comprises an ultraviolet (UV) lamp.

Figure 8:
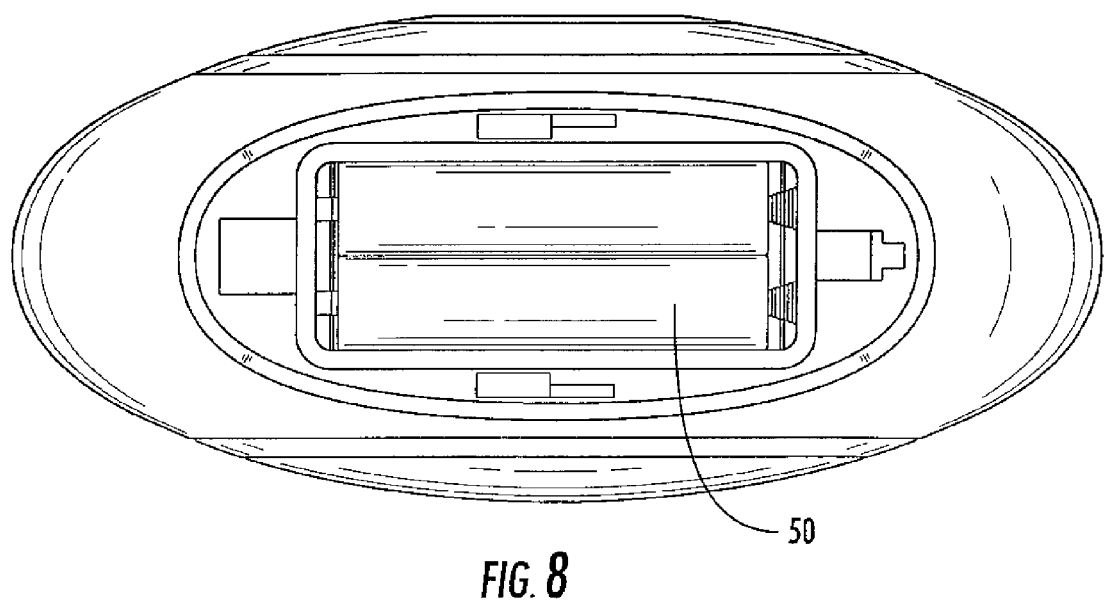
FIG. 8 is a bottom view of the sanitizing device illustrating an open battery compartment.

FIG. 8 is a bottom view of the sanitizing device 10 illustrating an open battery compartment 50. The device requires a power source to provide power to the UV lamp. Preferably, the device is battery operated. However, the device could be electrically wired to be plugged into an electrical outlet. The electrical control portion of the device comprises components such as a PC Board, the IC, timer circuit, and battery harness. Other various features of the present invention include, but are not limited to, the power button comprising an LED that flashes blue during the sanitizing operation. The power button may also flash red to indicate a low battery. The power button is preferably set in a recessed manner so as to avoid being inadvertently hit inside a suitcase during travel, for example, which would cause the battery to run down prematurely.

The UV lamp is powered on for a predetermined period of time suitable to sanitize the dental appliance with the UV light. The predetermined period of time is preferably in a range of about 5 to 10 minutes, more preferably eight minutes. The predetermined period of time begins once the UV lamp of the device is powered on such as by pressing a button or turning on a switch. Preferably, a button 3 connected to the power source is used to power on the device. Preferably, the button 3 is located on the exterior of the device as shown in FIG. 1.

Figure 9:
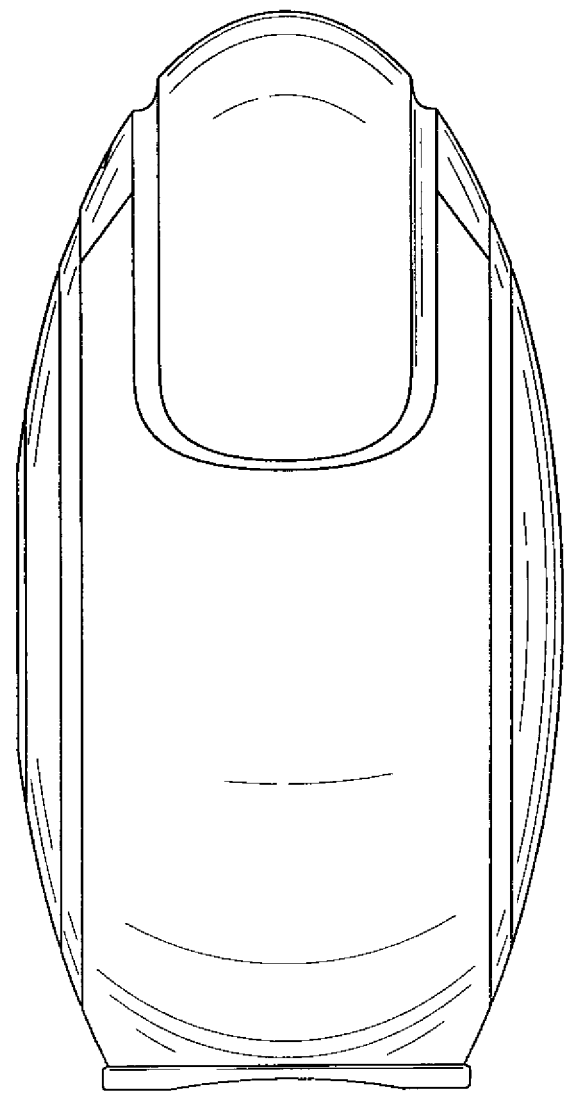
FIG. 9 is a side view of the sanitizing device in accordance with the present invention.

FIG. 9 illustrates a side view of the sanitizing device 10.

In a preferred aspect of the present invention, the device comprises a removable tray 60 for containing the removable dental appliance. The removable tray 60 is to be lifted in and out of the vertical slot of the sanitizing device, and there are vertically extending walls on opposing sides of the vertical slot between which the removable tray 60 is inserted.

Figure 10:
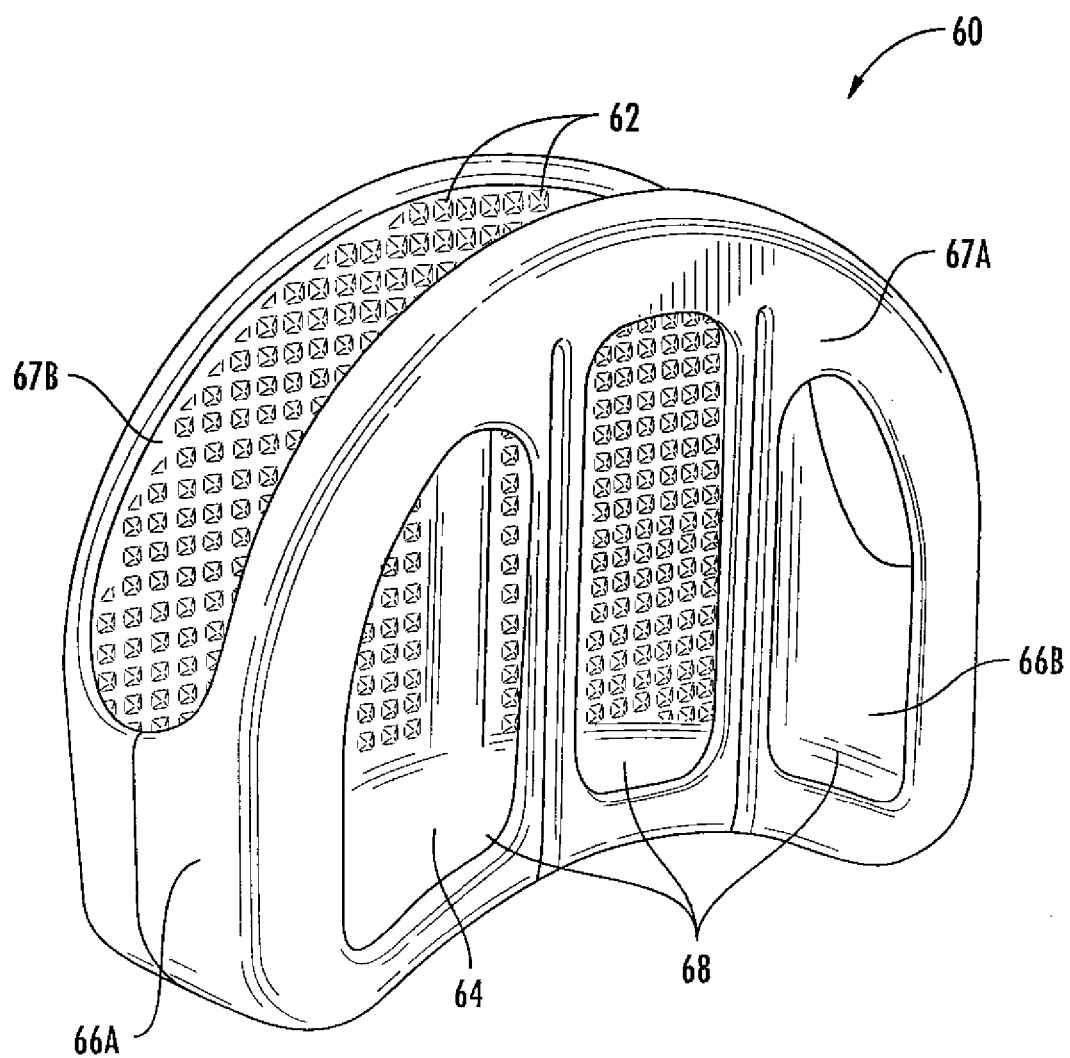
FIG. 10 is an angled front perspective view of a removable tray for use insertion in the vertical slot of the sanitizing device of the present invention.

FIG. 10 is an angled front perspective view of the removable tray 60 for use in accordance with the sanitizing device 10 of the present invention. As shown in FIG. 10, the removable tray 60 is comprised of a bottom 64 and at least two sides 67A and 67B. Preferably, the side 67A of the removable tray 60 adjacent to the UV lamp comprises at least one opening 68. Preferably, the removable tray 60 has a reflective inner surface or surfaces. In another aspect of the present invention, the removable tray comprises a multi-dimensional geometric pattern 62 which has the appearance of raised bumps on the reflective surface. A benefit of the removable tray having such features is to provide for the light emitted from the UV lamp to enter the removable tray and to reflect at various angles on the dental appliance inside the reflective tray in order to maximize the sanitizing effect of the device. The raised pattern, for example, facilitates the scattering of the ultraviolet light so that it better reaches all of the surfaces of the dental appliance being sanitized. The multi-dimensional geometric pattern varies the angle of incidence so that the angles of reflection are more varied. The multi-dimensional aspect of the pattern assists in holding the dental appliance away from the tray surfaces so that light can reach under and around all surfaces of the dental appliance.

Figure 11:
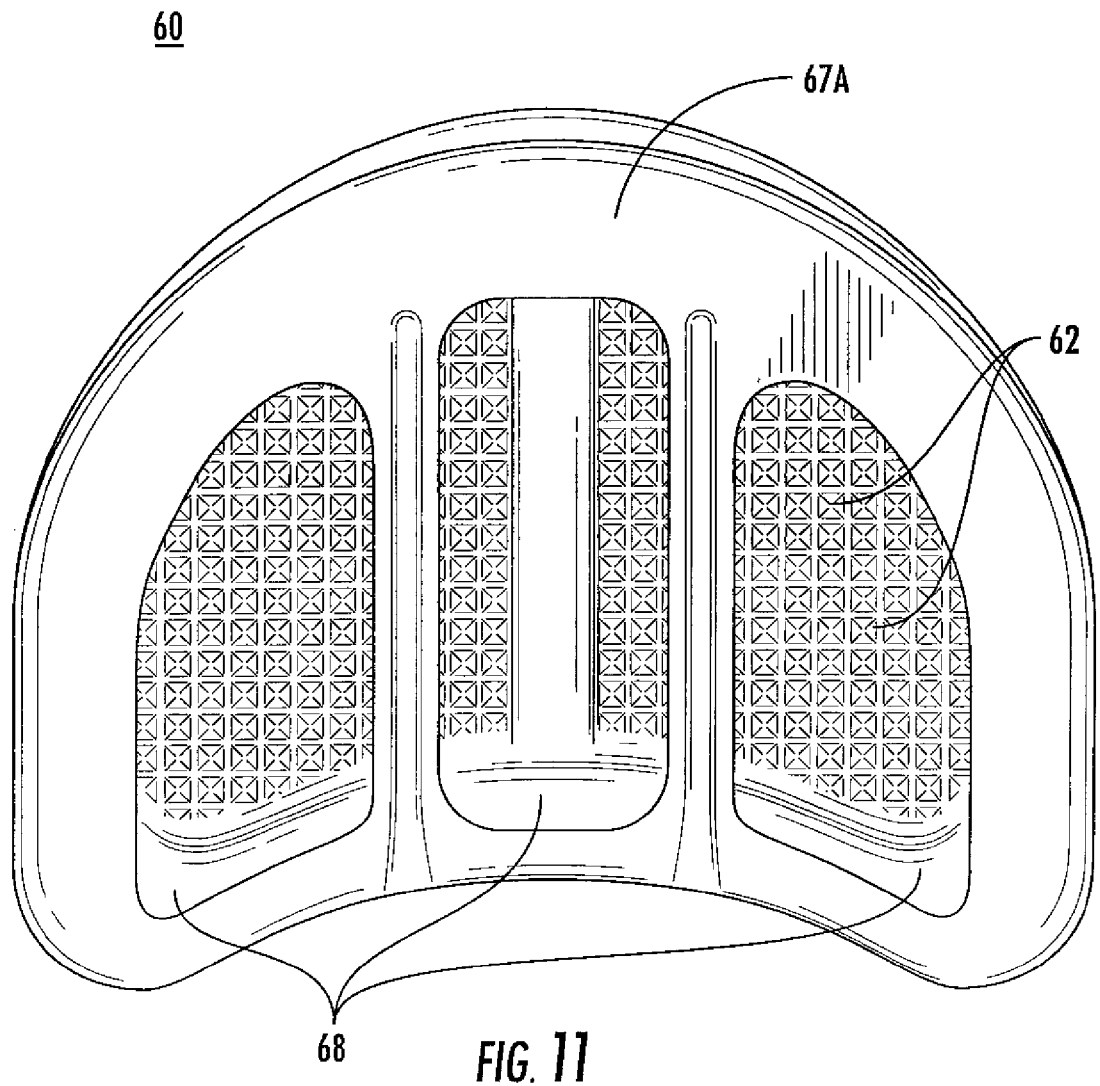
FIG. 11 is a front view of a removable tray suitable for use in accordance with the present invention.
Figure 12:
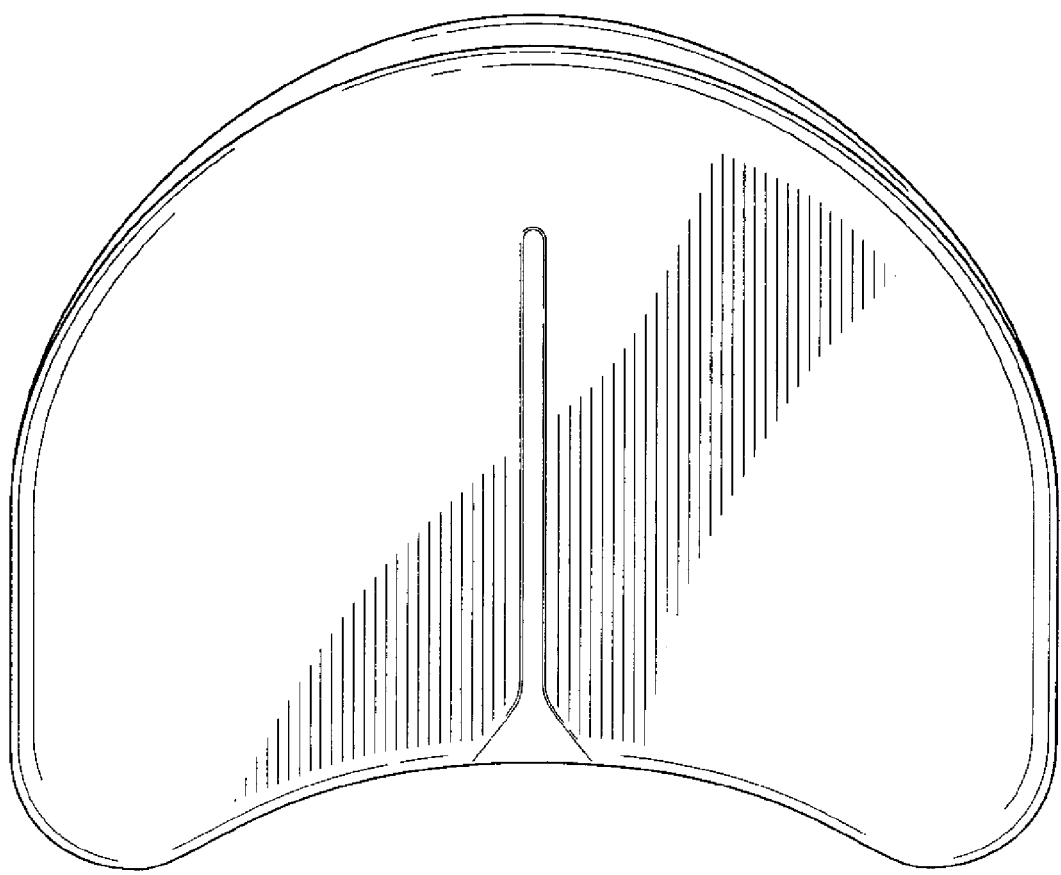
FIG. 12 is a back view of a removable tray suitable for use in accordance with the present invention.

FIG. 11 is a front view of a removable tray 60 suitable for use in accordance with the device of the present invention. FIG. 12 is a back view of a removable tray 60 suitable for use in accordance with the device of the present invention.

Figure 13:
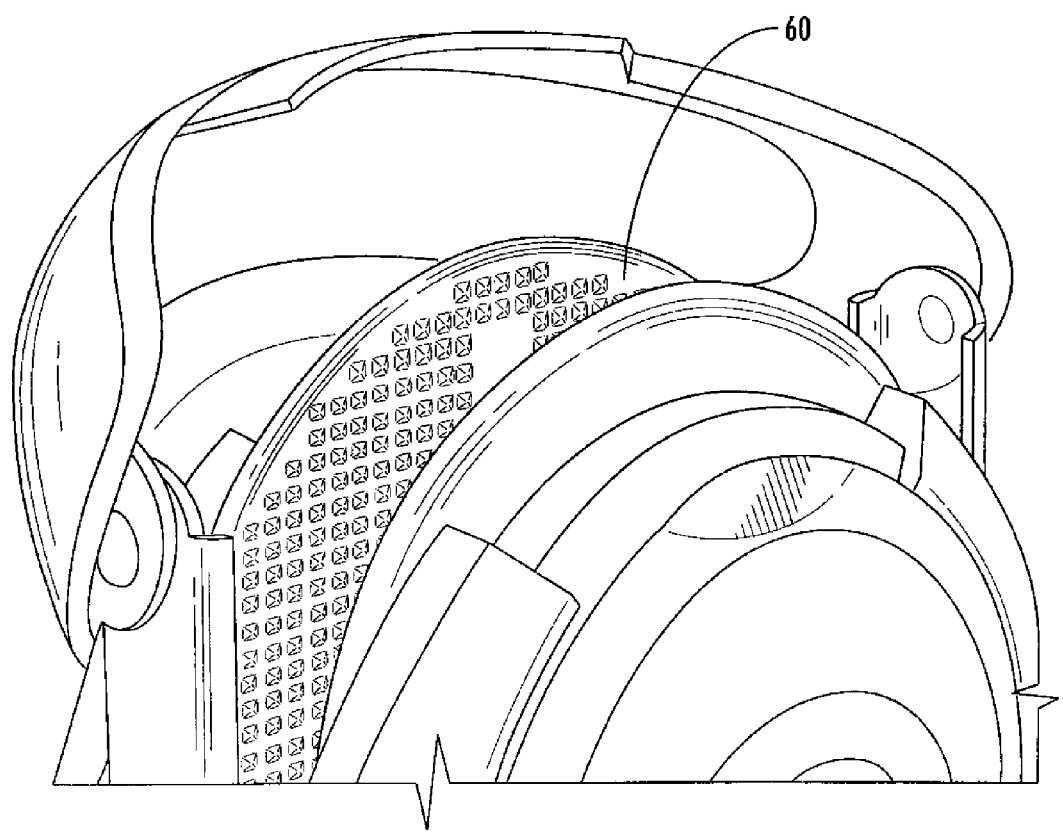
FIG. 13 is an angled partial front perspective view of the sanitizing device of the present invention with removable tray inserted in the sanitizing device of the present invention.

FIG. 13 is an angled partial front perspective view of the sanitizing device of the present invention with removable tray 60 inserted in the vertical slot of the sanitizing device of the present invention.

Figure 14:
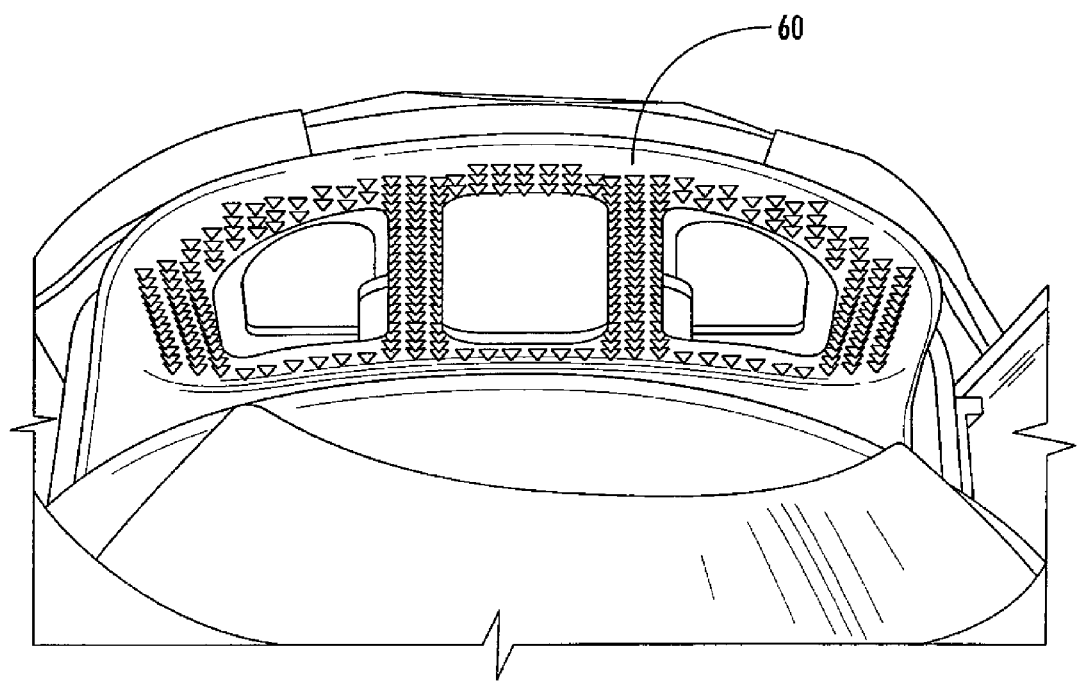
FIG. 14 is a partial top perspective view of the sanitizing device of the present invention with removable tray inserted in the sanitizing device of the present invention.

FIG. 14 is a partial top perspective view of the sanitizing device of the present invention with removable tray 60 inserted in the vertical slot of the sanitizing device of the present invention.

Figure 15:
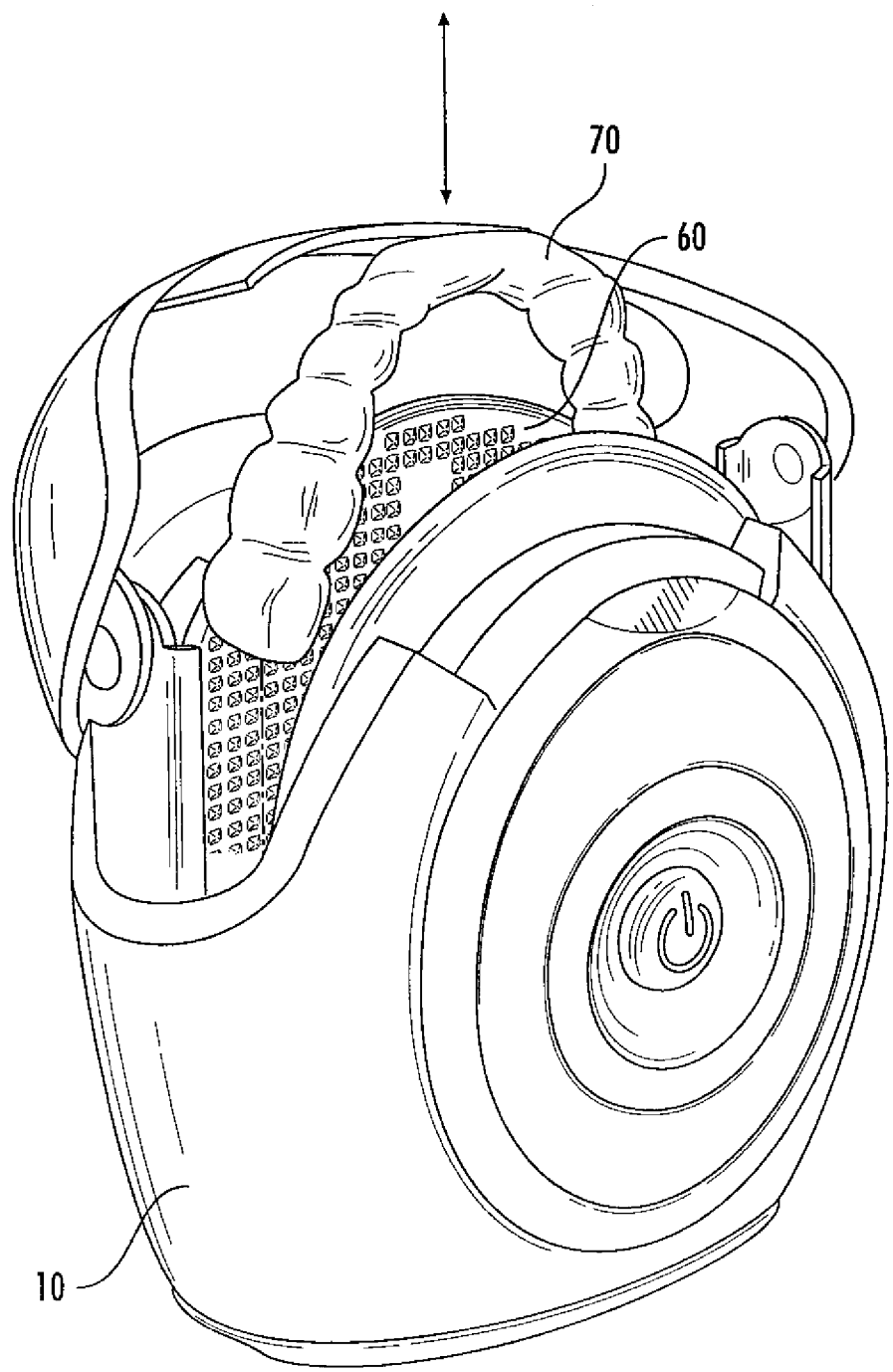
FIG. 15 is an angled front perspective view of the sanitizing device of the present invention with inserted removable tray illustrating the removable dental appliance being inserted into the removable tray.

FIG. 15 is a front angled perspective view of the sanitizing device 10 of the present invention with inserted removable tray 60 illustrating the removable dental appliance 70 being inserted in the removable tray 60.

Advantages exist with the device of the present invention. An advantage of the device of the present invention is that the dental appliance is flooded with UV light for a predetermined period of time such as a period of minutes before the light turns off automatically. It is possible for the dental appliances to remain inside the sanitizing device until worn, thereby also solving the problem of sanitary storage. An advantage of the battery-powered device is that it makes the device portable. A reflective tray ensures that the UV light reaches the front and back surfaces of the dental appliance inside. Another advantage of the removable tray is that it can be removed for washing to allow the interior portion of the tray that comes in contact with the dental appliance to be cleaned periodically, if desired. Other features of the device include an automatic timer and safety shut-off.

EXAMPLE

The device was tested in independent testing by a national laboratory in accordance with USFDA regulations (21 CFR Part 58) to determine the efficacy of the sanitizing device against representative challenge organisms. Each organism configuration was tested as a dry challenge on representative coupons. Each combination was tested in duplicate with positive controls for every organism and surface tested. Rigid PVC retainer material was tested in the UV light of the sanitizing device of the present invention for an approximately eight (8) minute cycle. Results of the testing indicated that the device of the present invention was effective to kill over 99.9% of common bacteria and microorganisms that can cause or extend illness and oral infection including, but not limited to, staphylococcus aureus, *escherichia coli*, *salmonella choleraesuis*, *streptococcus pyogenes* and *candida albicans*. Results are shown in Table 1 and in the attached report.

TABLE 1

| ORGANISM (American Type Culture Collection-ATCC) | AVERAGE CONTROL TITER (COLONY FORMING UNITS/COUPON) | AVERAGE RECOVERY (CFU/COUPON) | PERCENT REDUCTION (%) | $\text{Log}_{10}$ REDUCTION |
|---|---|---|---|---|
| *Staphylococcus aureus* (ATCC #6538) | $2.2 \times 10^6$ | $<2.0 \times 10^2$ | >99.9910 | >4.04 |
| *Pseudomonas aeruginosa* (ATCC #15442) | $6.2 \times 10^6$ | $<2.0 \times 10^2$ | >99.9968 | >4.49 |
| *Escherichia coli* (ATCC #11229) | $3.2 \times 10^6$ | $<2.0 \times 10^2$ | >99.9937 | >4.20 |
| *Salmonella choleraesuis* (ATCC #19615) | $3.4 \times 10^6$ | $<2.0 \times 10^2$ | >99.9941 | >4.23 |
| *Streptococcus pyogenes* (ATCC #19615) | $3.2 \times 10^6$ | $\sim3.7 \times 10^2$ | ~99.989 | ~3.95 |
| *Candida albicans* (ATCC #10231) | $5.4 \times 10^6$ | $<2.0 \times 10^2$ | >99.9963 | >4.43 |

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements.

What is claimed is:

1. A device for sanitizing a removable dental appliance, the device comprising:
    a vertical slot for insertion of a removable dental appliance in a sanitizing device,
    a removable tray for containing the removable dental appliance, and
    vertically extending walls on opposing sides of the vertical slot, wherein one of the vertically extending walls comprises an ultraviolet lamp.

2. The device according to claim 1, wherein the ultraviolet lamp is in a U-shaped configuration.

3. The device according to claim 2, wherein the U-shaped configuration is inverted.

4. The device according to claim 1, further comprising a lid.

5. The device according to claim 4, wherein the lid is connected by a hinge to a retractable arm connected to the device.

6. The device according to claim 5, wherein the hinged lid is pivotable in a forward direction, backward direction, or a combination thereof.

7. The device according to claim 1, wherein the device comprises at least one opening in an inner wall of the device.

8. The device according to claim 4, wherein the lid comprises an inner side having a reflective surface.

9. The device according to claim 1, wherein the device further comprises a power source.

10. The device according to claim 9, wherein the power source is activated by a button on the device.

11. A device for sanitizing a dental appliance, the device comprising:
- a vertical slot in a sanitizing device,
- a removable tray for containing a removable dental appliance, the removable tray to be lifted in and out of the vertical slot of the sanitizing device, wherein the removable tray has a reflective surface and comprises a multi-dimensional geometric pattern, and
- vertically extending walls on opposing sides of the vertical slot between which the removable tray is inserted, wherein one of the vertically extending walls comprises an ultraviolet lamp.

12. The device according to claim 11, wherein the ultraviolet lamp is in a U-shaped configuration.

13. The device according to claim 12, wherein the U-shaped configuration is inverted.

14. The device according to claim 11, wherein the removable tray has a side comprising at least one opening.

15. A removable tray for use in a dental appliance sanitizing device, the removable tray comprising at a bottom and at least two sides, wherein at least one of the sides of the removable tray has a reflective surface.

16. The removable tray according to claim 15, wherein at least one of the sides further comprises a multi-dimensional geometric pattern.

17. The removable tray according to claim 15, wherein at least one of the sides comprises at least one opening.

18. The removable tray according to claim 15, wherein the removable tray is in a U-shaped configuration.

* * * * *